(12) United States Patent
Robbins

(10) Patent No.: US 6,787,105 B2
(45) Date of Patent: Sep. 7, 2004

(54) PROCESS AND APPARATUS FOR REDUCTION OF MICROORGANISMS IN A CONDUCTIVE MEDIUM USING LOW VOLTAGE PULSED ELECTRICAL ENERGY

(76) Inventor: John A. Robbins, 1814 Commerce Ave., Suite A, Vero Beach, FL (US) 32960

( * ) Notice: Subject to any disclaimer, the term of this patent is extended or adjusted under 35 U.S.C. 154(b) by 456 days.

(21) Appl. No.: 10/017,383

(22) Filed: Dec. 18, 2001

(65) Prior Publication Data

US 2002/0168456 A1 Nov. 14, 2002

Related U.S. Application Data

(63) Continuation-in-part of application No. 09/557,963, filed on Apr. 25, 2000, now Pat. No. 6,331,321.

(51) Int. Cl.[7] .............................. A61L 2/00; B01J 19/00; A61M 1/14; A01K 43/00; A21D 6/00
(52) U.S. Cl. ............................... 422/22; 422/1; 422/38; 422/40; 422/44; 422/292; 422/300; 422/307; 426/231; 426/237
(58) Field of Search ............................... 422/1, 22, 38, 422/40, 44, 292, 300, 307, 900, 905; 426/231, 237

(56) References Cited

U.S. PATENT DOCUMENTS

| | | | |
|---|---|---|---|
| 4,315,514 A | 2/1982 | Drewes et al. | 128/653 |
| 4,457,221 A | 7/1984 | Geren | 99/451 |
| 4,695,472 A | 9/1987 | Dunn et al. | 426/237 |
| 4,838,154 A | 6/1989 | Dunn et al. | 99/451 |
| 4,871,559 A | 10/1989 | Dunn et al. | 426/248 |
| 4,917,785 A | 4/1990 | Juvan | 204/164 |
| 4,957,606 A | 9/1990 | Juvan | 204/164 |
| 4,994,160 A | 2/1991 | Doevenspeck | 204/165 |
| 5,026,484 A | 6/1991 | Juvan | 210/717 |
| 5,034,235 A | 7/1991 | Dunn et al. | 426/238 |
| 5,037,524 A | 8/1991 | Juvan | 204/307 |
| 5,048,404 A | 9/1991 | Bushnell et al. | 99/451 |
| 5,091,152 A | 2/1992 | Thomas, Sr. | 422/23 |
| 5,235,905 A | 8/1993 | Bushnell et al. | 99/451 |
| 5,324,398 A | 6/1994 | Erickson et al. | 204/149 |
| 5,364,645 A | 11/1994 | Lagunas-Solar et al. | 426/248 |
| 5,368,724 A | 11/1994 | Ayers et al. | 210/110 |
| 5,393,541 A | 2/1995 | Bushnell et al. | 426/237 |
| 5,397,961 A | 3/1995 | Ayers et al. | 315/111.21 |
| 5,447,733 A | 9/1995 | Bushnell et al. | 426/237 |
| 5,464,513 A | 11/1995 | Goriachev et al. | 204/164 |
| 5,514,391 A | 5/1996 | Bushnell et al. | 426/237 |
| 5,549,041 A | 8/1996 | Zhang et al. | 99/451 |
| 5,630,915 A | 5/1997 | Greene et al. | 204/164 |
| 5,690,978 A | 11/1997 | Yin et al. | 426/237 |
| 5,766,447 A | 6/1998 | Creijghton | 205/742 |
| 5,768,853 A | 6/1998 | Bushnell et al. | 53/167 |
| 5,776,529 A | 7/1998 | Qin et al. | 426/231 |
| 5,786,598 A | 7/1998 | Clark et al. | 250/455 |
| 5,801,489 A | 9/1998 | Chism, Jr. et al. | 315/111.21 |
| 5,837,303 A | 11/1998 | Hayden | 426/237 |
| 5,900,211 A | 5/1999 | Dunn et al. | 422/24 |
| 5,925,885 A | 7/1999 | Clark et al. | 250/492.1 |

(List continued on next page.)

OTHER PUBLICATIONS

FDA Submission by John Robbins Published Apr. 29, 1999, including letter from J. Robbins to FDA dated Sep. 30, 1998, Appendices I–V and Appendix A.

(List continued on next page.)

Primary Examiner—Terrence R. Till
Assistant Examiner—Monzer R. Chorbaji
(74) Attorney, Agent, or Firm—Wenderoth, Lind & Ponack, L.L.P.

(57) ABSTRACT

A process and apparatus are provided for reducing microorganisms in a conductive medium using a low voltage pulsed electrical energy.

38 Claims, 2 Drawing Sheets

U.S. PATENT DOCUMENTS

| | | | |
|---|---|---|---|
| 6,010,613 A | 1/2000 | Walters et al. | 205/701 |
| 6,010,727 A | 1/2000 | Rosenthal | 426/240 |
| 6,013,918 A | 1/2000 | Bushnell et al. | 250/454.11 |
| 6,019,031 A | 2/2000 | Qin et al. | 99/451 |
| 6,027,754 A | 2/2000 | Bushnell et al. | 426/238 |
| 6,078,490 A | 6/2000 | Walters | 361/88 |
| 6,086,932 A | 7/2000 | Gupta | 426/237 |
| 6,093,432 A | 7/2000 | Mittal et al. | 426/237 |
| 6,110,423 A | 8/2000 | Bushnell et al. | 422/23 |
| 6,117,660 A | 9/2000 | Walters et al. | 435/173.6 |
| 6,120,818 A | 9/2000 | Long | 426/238 |
| 6,150,663 A | 11/2000 | Rosenthal | 250/435 |
| 6,168,814 B1 | 1/2001 | Long | 426/238 |
| 6,178,880 B1 | 1/2001 | Mastwijk et al. | 99/451 |
| 6,214,297 B1 | 4/2001 | Zhang et al. | 422/186 |
| 6,228,266 B1 | 5/2001 | Shim | 210/614 |
| 6,228,332 B1 | 5/2001 | Dunn et al. | 422/186.3 |

OTHER PUBLICATIONS

Pulsed Power Odor Control of a Power Plant Intake Dredging Project, Vero Beach Municipal Power Plant, Dec. 1997.

Food Engineering, "Pulse power disinfects fresh juices, extends shelf life", Oct. 1998, pp. 47–49.

Appendix I to J. Robbins FDA submission, Bai–Lin Qin et al., "Inactivating Microorganisms Using a Pulsed Electric Field Continuous Treatment System", IEEE Transactions on Industry Applications, vol. 34, No. 1, Jan./Feb. 1998.

Appendix II to J. Robbins FDA submission, Karl H. Schoenbach et al., "The Effect of Pulsed Electrical Fields on Biological Cells", paper presented at EPRI/Army PEF Workshop II, Chicago, IL on Oct. 10–11, 1997.

Appendix III to J. Robbins FDA submission, K. H. Schoenbach et al., Effect of Pulsed Electric Fields on Micro–organisms: Experiments and Applications, paper presented at EPRI/Army PEF Workshop II, Chicago, IL on Oct. 10–11, 1997.

Appendix IV to J. Robbins FDA submission, K. H. Schoenbach et al., "The Effect of Pulsed Electric Fields on Biological Cells: Experiments and Applications", IEEE Transactions on Plasma Science, vol. 25, No. 2, Apr. 1997.

Appendix I to J. Robbins FDA submission, Minutes of EPRI/Army PEF Workshop II, Chicago, IL on Oct. 10–11, 1987.

Appendix A to J. Robbins FDA submission, 28 Day Shelf Life Study on Orange Juice Treated Using Electric Pulse Process, Metals Analysis for Primary and Secondary Standards on Orange Juice Treated Using Electric Pulse Process.

PROCESS AND APPARATUS FOR REDUCTION OF MICROORGANISMS IN A CONDUCTIVE MEDIUM USING LOW VOLTAGE PULSED ELECTRICAL ENERGY

This application is a continuation-in-part of application Ser. No. 09/557,963 filed Apr. 25, 2000 now U.S. Pat. No. 6,331,321.

BACKGROUND OF THE INVENTION

1. Field of the Invention

A process and apparatus is provided for the reduction of microorganisms in a conductive medium using low voltage pulsed electrical energy.

2. Description of Related Art

Reduction of microorganisms in a medium using electricity has been studied for many decades. Most early efforts focused on the reduction of microorganisms in a medium by passage of a high voltage electric current through the medium to generate heat, thereby killing the microorganisms in the medium by pasteurization. The conductive medium was often a pumpable food or beverage, such as milk or water.

Later efforts focused on the reduction of the microorganisms by so-called "nonthermal" pasteurization methods. These methods involve application of a high voltage electric field to the medium in short pulses. The high voltage electric field generates an applied energy of 150 joules/ml or greater and causes death of the microorganisms by electroporation or lysis of the microbial cell membrane. The shortness of the pulse duration attempted to minimize heating of the medium. However, these methods suffer from numerous disadvantages, especially when applied to pumpable foods and beverages. For example, the high voltage electric field when applied to pumpable foods and beverages can cause structural alterations in the food or beverage, adversely effecting the taste and texture of the food or beverage. In addition, such high applied energies are believed to cause the formation of free radicals in foods and beverages, which compounds are considered to cause or promote cancer. Further, the equipment necessary to generate such high applied energies requires an electrical energy on the order of 100 kV/cm. Furthermore, such methods do not appear to kill all types of microorganisms, such as molds and yeast.

Experiments have been conducted in the prior art using low voltage electric fields. However, these electrical energy applications were considered to be unsatisfactory because they were not deemed to cause irreparable damage to the microorganisms.

As examples of the prior art, reference is made to the following U.S. patents, whose teachings are incorporated by reference: U.S. Pat. No. 4,917,785; U.S. Pat. No. 4,957,606; U.S. Pat. No. 5,026,484; U.S. Pat. No. 5,037,524; U.S. Pat. No. 5,464,513; U.S. Pat. No. 5,514,391; U.S. Pat. No. 5,630,915; U.S. Pat. No. 5,766,447; and the following publications: Bai-Lin Qin et al., "Inactivating Microorganisms Using a Pulsed Electric Field Continuous Treatment System", *IEEE Transactions on Industry Applications*, Vol. 34, No. 1, January/February 1998; Karl H. Schoenbach et al., "The Effect of Pulsed Electrical Fields On Biological Cells", paper presented at EPRI/Army PEF Workshop II, Chicago, Ill. on Oct. 10–11, 1997; K. H. Schoenbach et al., "Effect of Pulsed Electric Fields on Micro-organisms: Experiments and Applications, paper presented at EPRI/Army PEF Workshop II, Chicago, Ill. on Oct. 10–11, 1997; and Karl H. Schoenbach et al., "The Effect of Pulsed Electric Fields on Biological Cells: Experiments and Applications", *IEEE Transactions on Plasma Science*, Vol. 25, No. 2, April 1997.

SUMMARY OF THE INVENTION

The process of this invention improves on the prior art by providing a method of microbial reduction in a conductive medium which affects the target microorganism(s) without causing detrimental effects to the medium. The term "reduction" is used in its conventional sense in the art to mean that the method results in mortality to some or all target organisms. In other words, after treatment with the method of this invention, the treated medium contains a substantially decreased number of viable microorganisms. Applications include conductive mediums such as pumpable foods, beverages, processing fluid streams, blood, water, and ecosystem waters, as well as conductive solids and solids suspended in liquids or gases to include air, which mediums are microbiologically infected and capable of causing harm to those consuming or coming in contact with the infected medium. The term "pumpable foods" means any food which is capable of being pumped or conveyed through pipes or conduits, including solid food items conveyed in a conductive aqueous solution. Examples of solid food items in this later category are fruits and vegetables. Conductive solids means any solid item capable of being pumped or conveyed through pipes, conduits or channels. Examples in this category are powderized materials. Suspended solids means any solid suspended in a liquid or gas. Examples in this category are food items in carrier liquids or volatile suspended solids in a wastewater facility.

The method of this invention involves the application of low voltage pulsed electrical energy having defined voltage, frequency and pulse waveform characteristics to the target microorganisms in the medium. By the term "low voltage pulsed electrical energy", it is meant that the combination of energy, frequency and pulse waveform applied to the microorganisms must be such that no free radicals are formed, no ionizing radiation is created, and no osmotic shock waves are formed. The term "low energy pulses" which is used herein by the inventor has the same meaning. It is surprising that the low energy pulses result in cell mortality, since the energy pulses are too low to cause electroporation or lysis of the microbial cell membrane. The specific mechanism by which the method of this invention causes mortality of the microorganisms is not clearly understood. One theory is that the low energy pulses of specific voltage, frequency and pulse waveform cause a disruption in an essential component of the intricate cellular machinery of the microorganism, such as a disruption of the metabolic and/or respiration cycles of the target microorganism. Regardless of exactly how the method of this invention operates to cause mortality to microorganisms, the inventor has demonstrated through extensive experimental tests which are summarized herein that the method is surprisingly effective. Accordingly, when the method is applied with the proper know-how described herein, the ordinary skilled person can achieve substantial reductions in target organisms in a conductive medium by application of low energy pulses which do not have detrimental effects on the medium. As an example of detrimental effects to a medium, there is mentioned the occurrence of organo-leptic changes to a medium which is a pumpable food or beverage.

The effective voltage, pulse frequency and waveform characteristics of each target organism are unique, and therefore the process requires the ability to vary the frequency of energy delivery as well as to vary the voltage applied, with a limitation being such that no combination of applied voltage, pulse frequency and waveform applied is capable of creating structural membrane alterations of the target organisms, e.g., electroporation or lysation of the target organism. Additionally, the combination of energy, pulse frequency and waveform applied must be such that no free radicals are formed, no ionizing radiation is created, nor osmotic shock waves formed. Further, there is substantially no temperature increase or pressure increase.

This process improves on the prior art of disinfection by affecting only the target organism, not the medium. This is accomplished by the controlled release of pulsed energy into a treatment space, such as a conduit or chamber. The process and apparatus may provide for multiple treatment spaces in continuous parallel or series flow paths. The process and apparatus may be installed in a continuous flow production line or in a container, such as a batch storage tank.

The combination of voltage, pulse frequency and pulse waveform are refined such that the energy applied to the target organism disrupts the respiration and/or metabolic codes of the target organism thereby killing the organism. As metabolic and respiration codes are required for living organisms to function, disruption of the codes cause the elimination of the reproductive cycle and death. Surprisingly, the process of the present invention is even capable of killing microorganisms, such as molds and yeast, which are not effected by high voltage electric field methods.

As the voltage, pulse frequency and pulse waveform of the pulsed electrical energy are control parameters, it is preferable to incorporate monitoring with process control into the overall process design to accomplish commercial viability by insuring process consistency, operator safety and documentation of treatment.

Preferably, the parameters to be monitored and controlled which are incorporated into the process design are flow rate of the medium, conductivity of the medium, pH of the medium, pressure of the medium, temperature of the medium, voltage potential between the cathode and anode electrodes of the pulser, current generated by the electrodes into the medium, frequency of the electric pulse, the shape and amplitude of the electric pulse which define the pulse waveform, and the applied energy which is exerted on the microorganisms in the particular medium.

It is specifically noted the process and apparatus described herein are those which represent an improvement in the art. The individual physical components of the apparatus used in the process of the invention, such as pipes, wires, switches, power supplies, pursers, sensors and computers, are currently in existence or can be manufactured by the ordinary skilled artisan using available components. It is the specific way in which these existing components are organized into the apparatus of the invention, and the actual process method for microorganism reduction, that represent the improvement to prior art.

Process Method and Apparatus

The process method provides for a flow of medium/product to enter and exit a treatment space whereby, while in the treatment space, energy is pulsed into the treatment space via DC electric pulses at a defined voltage, pulse frequency and pulse waveform, which is capable of disrupting the control mechanisms of target organisms. Preferably the flow of medium/product into the treatment space, and its treatment thereof, is a continuous process. Many commercial processes require a continuous flow operation, such as the production process for making a fresh citrus juice. The process and apparatus of this invention are ideally suited for such processes, because the invention may be installed in the continuous flow operation, be used to effectively reduce the naturally occurring microorganisms in the juice, without hindering the speed or arrangement of the normal flow operation. Alternatively, the process is suitable for treatment of microorganisms in a non-continuous flow operation, such as the treatment of medium in a container. For example, control of microorganisms in a batch storage tank is often a problem. The medium contained in the batch storage tank such as juice in a large storage tank or liquids stored at the base of a cooling tower may be circulated through the apparatus of this invention and the microbial content may be reduced using the process of this invention.

The treatment space may be an area of any shape and size which is suitable for holding a conductive medium and subjecting it to low pulsed energy. Preferably the treatment space is defined by the walls of a chamber, the chamber being a partially enclosed space having an inlet and an outlet which are connected to conduits for passing the medium through the chamber for treatment. Within the chamber are at least one pair of electrodes for generating the low pulsed energy. Alternatively, the treatment space may be an area within a conduit itself, such that the treatment space is not enclosed except as defined by the conduit wall and is open to flow of the medium therethrough. The pair of electrodes are inserted through the conduit wall for generating the low pulsed energy within the conduit.

The pair of electrodes are connected by electrical cables to a pulse modulation unit, also referred to herein as a pulser unit or pulser. The pulse modulation unit contains the electrical components, i.e. capacitors, waveform generators, AC to DC transformers, etc., for generating the low voltage electrical pulses, by applying a defined DC voltage to the pair of electrodes, and generating a defined pulse waveform at a defined pulse frequency. Pulse modulation units are commercially available. Preferably the pulse modulation unit is not limited in operation to a single defined voltage, frequency and waveform but is capable of adjustment of these parameters as necessary or desired by the operator. The pulse modulation unit may be proximate or remote from the pair of electrodes. The pulse modulation unit is connected by electrical cables to an AC electrical energy source.

As each family of organisms is different, the metabolic components of the organism, and the information communicated within the organism such as in the form of coded electrical pulses, are also different. Therefore, the process control settings of the invention are required to be variable so as to provide treatment to different organism types within various medium/product.

The process is controlled by a central processing unit (CPU), which may either be a component of the pulse modulation unit or be separate therefrom. The CPU will be programmed to set operating limits for all control parameters. The principle control parameters are pulse frequency, pulse waveform (pulse shape and amplitude) and level of applied voltage.

The pulse frequency may range from 1 to 1000 pulses per second, preferably 60 to 180 pulses per second, more preferably about 120 pulses per second (i.e. 120 Hz).

The pulse waveform is defined by the pulse shape and pulse amplitude. The pulse shape may be any shape, e.g. monopulse, bipulse, bipolar, sine wave, spike, square, etc. Preferably the pulse shape is a monopulse in the positive domain. The pulse amplitude may be in the range of 6,000 V to 15,000 V, more preferably about 12,000 V.

The applied voltage is not limited but may be any suitable voltage which is capable of generating a low voltage pulsed electrical energy into the medium capable of reducing the microorganisms therein, without the formation of free radicals in the medium, without creation of osmotic shock in the medium, and without the generation of ionizing radiation such as lethal UV radiation in the medium.

The amount of applied energy is more critical to the invention than the applied voltage. The applied energy essentially means the amount of energy reaching the target organism in the medium. The applied energy varies based upon the conductivity or resistance of the medium. Thus, a medium having a higher resistance will require a higher voltage in order to generate the same level of applied energy. Furthermore, different organisms are sensitive to different levels of applied energy. Hence a target microorganism must be tested in the medium in which it will be treated to determine the optimum voltage (as well as the optimum frequency and waveform characteristics), and thus the optimum level of applied energy, to kill the organism. For most food and beverage applications, the amount of applied energy must be less than or up to 1 joule/ml. For blood the applied energy would be as minimal as possible to kill the target organisms. The limits of applied energy may be obtained by optimizing the control parameters. For water and other applications, the amount of applied energy is not so limited, but may desirably be so limited if effective against the organism to be killed.

The amount of applied energy is affected by the flow rate of medium/product through the treatment chamber. The flow rate may be in the range of 1 to 300 gallons per minute, preferably in the range of 15 to 25 gallons per minute, more preferably about 20 gallons per minute. For blood treatment the flow rate may be much less than 1 gallon per minute, when the invention is used in similar fashion to a dialysis, or at higher rates when treating large volumes such as those at blood banks.

As noted above, the key aspects of the pulsed electric energy which result in mortality of the microorganism are the applied voltage, frequency and pulse waveform, which subject the target microorganism to a lethal applied energy. Since these key aspects are a function of the medium in which the target organism is contained, it is preferable to monitor and control additional control parameters. Preferably the process and apparatus of the invention monitors and controls the following parameters: 1) flow rate—is related to the number of pulses required to kill an organism type and determines the number of reaction chambers in series required to kill the target organism; 2) conductivity—relates to the ease of pulse travel through the medium; 3) pH—assists in verification the medium has not changed characteristics; 4) pressure—is monitored for verification of consistency in flow rate of medium thereby helping to ensure consistent delivery of uniform energy per unit volume of product; 5) temperature—is monitored to ensure the applied energy has remained within design limits without raising the temperature of the medium; 6) voltage—the AC power supply is monitored, and DC voltage is monitored across the electrical pulse delivery system for verification of consistent energy delivery; 7) current—is monitored along with voltage monitoring of the electrical pulse power supply to ensure consistent energy feed conditions for consistent treatment effects; 8) electrical pulse frequency—is monitored to determine consistent energy per unit volume of medium/product is obtained; 9) pulse shape—is monitored across the electrical pulse delivery unit to ensure consistent treatment.

Process Control

The control of the process is such that high quality treated medium/product is tantamount. To accomplish this the process monitoring is also control based and interactive. The control system is designed/programmed for application specific environments. That is, each target organism as well as medium/product characteristic is examined to determine the appropriate level of applied energy, frequency and pulse shape necessary to achieve the desired level of microbial reduction in the medium.

It is contemplated that each application may be different and it is anticipated several iterations may be required in pilot studies to refine the final operating conditions. This process allows that flexibility with respect to control range settings of each process variable that is being monitored.

An examination of application installation/location will allow for a determination for the need for redundant or parallel installations of the process. The target organism and medium/product characteristics determine the number of treatment spaces or chambers to be placed in series so as to deliver the correct energy, pulse frequency and pulse shape per unit volume.

The disruption of the metabolic/respiration cycle of the target organism in a specific medium is viewed as a solution couple and must be viewed together. This is a key concept of the invention which is not recognized in the prior art. The amount of applied energy which is effective to achieve mortality of the target microorganism must be determined by measuring the applied energy which achieves mortality for the particular target organism(s) in the particular medium to be treated. Upon determination of optimum control variable ranges, the process control settings are programmed into the CPU.

The control system's programmable logic controllers are capable of storing operating data. The control system is equipped with an interactive communication modem which allows data stored within to be accessed from a remote location via telephone, cable or satellite links. This will also allow for system diagnostics to be performed from remote locations.

All control variable sensors monitoring flow rate, conductivity, pH, pressure and temperature are preferably on both inlet and outlet locations of the reactor chamber. Voltage, current, frequency of pulse and pulse shape are preferably monitored on the appropriate energy system; voltage and current on the AC and DC systems; frequency of pulse across the pulse delivery system and shape of the pulse off the pulse discharge system.

The PLC units for each sensed/monitored control variable are set to control ranges for each variable.

As one of the process objectives is to create a consistent medium/product, at any time any control variable exceeds a preset limit (e.g. high and low settings for flow rate, conductivity, pH, pressure, temperature) an alarm function (e.g. audible, visual and/or electronic) will activate. At any time current voltage, frequency of pulse, or pulses shape does not meet preset values the same alarm function activates. Alarm activation will result in closing of downstream medium/product conveyance system, opening of a downstream diversion path to a designated storage system for later return back to treatment system; recording of all alarm events; shut down and isolation of medium/product delivery system; perform diagnostics and await operator instructions; auto-dial operator via communication system interface in the event operator is off-site. In the application of blood treatment where blood is shunted from the patient through the treatment space and returned to the patient, any parameter out of scale would shut the treatment space off but allow the blood to continue flowing. The alarm function would alert the attendant of a malfunction.

Process Flow Schematic

FIG. 1 shows a process flow schematic which illustrates the sequence of process events in a preferred embodiment of the invention. As each application is most likely different, the medium/product and target organism couple will dictate the number of electric pulse treatment spaces to be placed in series. Applied energy characteristics in terms of voltage, frequency and pulse shape are generally less than or up to one joule/ml for most food and beverage applications to prevent structural changes to the medium/product. Other applications may not be so limited.

The process is adaptive in that a series of electric pulse reactors may be sequenced to achieve microbial reduction without increasing the applied energy per unit volume per pulse.

The process flow path allows for diversion in the event the medium/product does not receive optimum energy application and provides a method of medium/product recovery and retreatment. In-line blood treatment would not allow for diversion of blood. In the event of malfunction, the unit would shut off and alert the attendant.

Process Operation

The process operation is based on a controlled sequence of events. Normal operation passes medium/product through the pretreatment system required by the application; e.g., citrus juice processing would be preceded by culling, grading, disinfection of peel and extraction. The extracted juice would then be pumped through a series of treatment spaces or chambers. If the processing line were large enough or operated continuously, parallel process lines would be used to allow for maintenance and repairs.

The control panel modem interface allows for remote monitoring and control.

On normal operation the applied energy reduces the target organism in the treatment space or chamber and the medium/ product is pumped to storage for packaging, etc. If the system senses a fault, the electric valve to the treated medium/product storage tank closes and the electric divert valve to the untreated divert storage tank opens. After repairs, the untreated medium/product is pumped back to the treatment space or chamber.

Parallel operations in multiple production lines allows for continuous maintenance. Parallel production lines can be connected via a common feed header and isolated by electric valves so individual treatment spaces or chambers can be turned on and off via the CPU by establishing a sequencing routine within the control system.

Applications

The process described herein is one of microbial reduction of organisms within a conductive medium. The electric pulse process of the invention may be applied to any conductive fluid, conductive solid or suspended solid in a liquid or gas, preferably to pumpable foods and beverages. Other applications of the electric pulse process include for the reduction of micro-organisms in surface waters; for reduction of marine estuary facultative organisms for the purpose of environmental odor control; for reduction of micro-organisms in power plant cooling towers; for the microbiological reduction of volatile solids from wastewater facilities; for reduction of microorganisms in conductive solids such as in powderized materials; and for reduction of microorganisms in a suspended solid such as in solids suspended in a liquid or gas to include air.

DETAILED DESCRIPTION OF THE PREFERRED EMBODIMENT(S)

Figure 1:
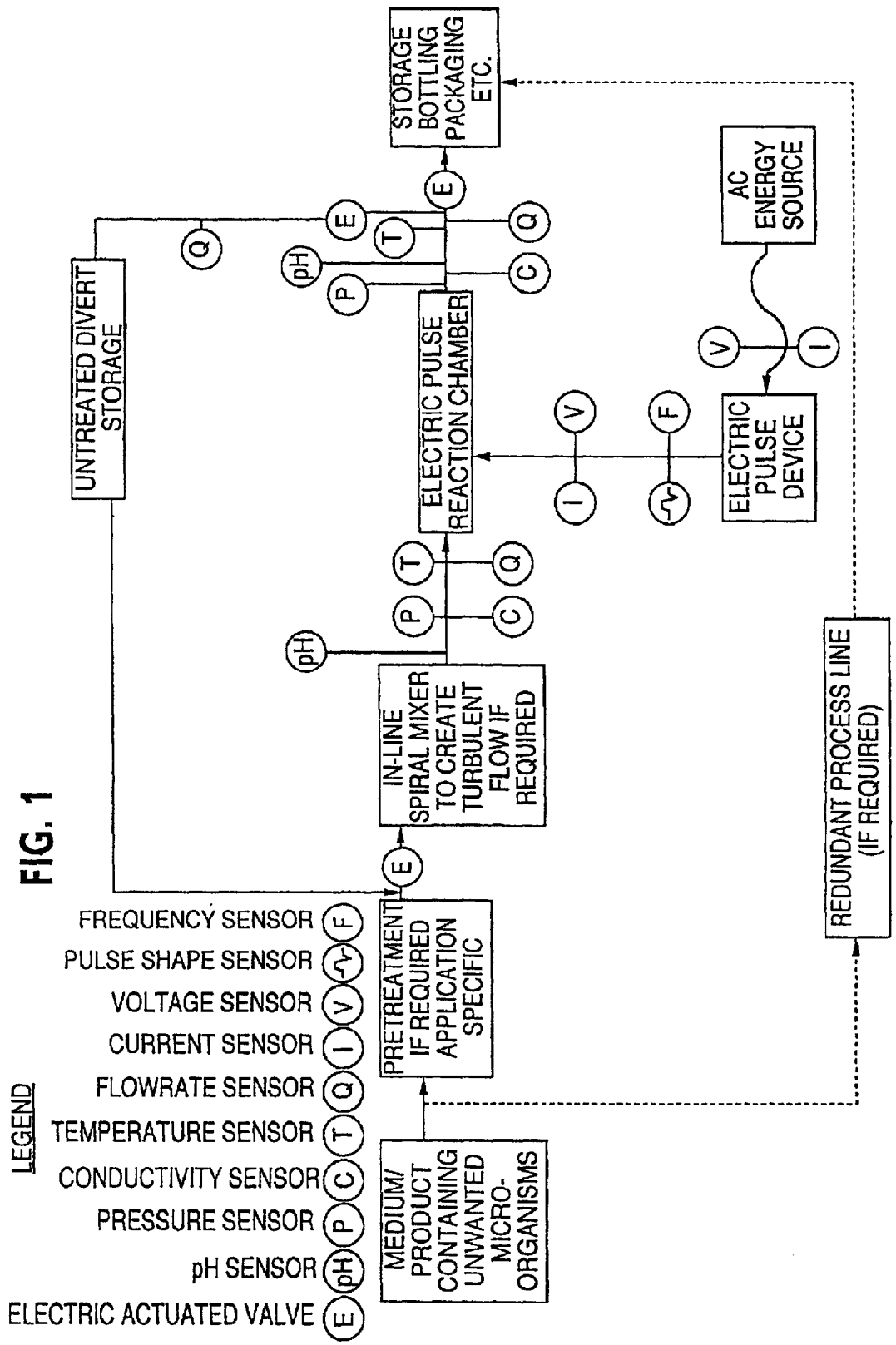
FIG. 1 shows a process flow schematic which is intended to illustrate the process and apparatus of the invention for reduction of microorganisms in a pumpable food using a continuous-flow treatment system.

A. Development of Pilot Study Program for Treatment of Juices

1. Project Objective

A pilot study was conducted to develop an effective non-thermal treatment system for juices. At the outset, it was necessary to fully establish the objectives of the project all the way through full scale commercialization. Therefore, discussions were held with many experts in the citrus industry and scientific community as well as regulatory agencies, marketing groups and food companies.

Based on many factors from varying points of view, a project/product objective was developed. The project would utilize existing components to generate electric pulses to treat juices without altering any of the characteristics associated with those of fresh squeezed juice. Additionally, it was decided orange and grapefruit juices were the first two juices to be produced. After testing, and regulatory acknowledgment, other juices would then be produced.

In order for the application of the electric pulse process to be commercially viable, it was decided that it must be more economical than thermal processes such as pasteurization and, from a consumer's point of view, provide a more nutritious food product. Additionally, the treatment technology itself must be accepted by the consumer. Further, the technology must be adaptable to meet performance standards such as those proposed by the juice warning label rule and possibly others in the future.

With the above in mind, a pilot testing program was initiated. All laboratory data used for certifications and validations was performed by qualified, certified and independent labs to include sampling.

2. Initial Testing to Establish Baseline Data

The first element of the pilot study consisted of determining which type of pulser and treatment space or chamber would optimize the reduction of micro-organisms without affecting the juice. Several different types of electric pulse modulation units and treatment chambers were and are today available commercially. Treatment chambers can produce electronic fields (E-fields) or they can produce electric pulses (submerged arc). A low energy electric pulser was selected. The pulser equipment was Model #PPS22 manufactured by Scientific Utilization, Inc., Huntsville, Ala. The pulser included pulse modulation equipment. Pulsers may be equipped with pulse modulation equipment or may be modified to include pulse modulation features by the artisan using known technology. Pulse modulation equipment can provide many different pulse shapes and pulse frequencies.

The purpose of the initial pilot tests was to establish baseline data with which modifications to the technology/ configurations could be accomplished.

The pulser selected provided multiple pulse wave forms and was capable of generating different pulse frequencies. The pulser selected was chosen because of its low energy density. The treatment chamber selected had a three-inch diameter inlet and outlet and thus provided adequate flow capacity.

Testing of the electric pulse system was conducted. A trailer-mounted system was located at a production facility in Florida and a side stream was created off the production line of this processing facility to begin testing fresh squeezed, non-pasteurized juice.

The initial tests were conducted with a single treatment chamber. A battery of laboratory tests were performed. The single chamber system was tested at 20 gallons per minute and at two different pulse frequencies. After review of the data it was concluded the electric pulse system was capable of reducing the background micro-flora of fresh juice.

It was concluded by review of the plate count data, it would be possible to increase the microbial reductions by placing two treatment chambers in series.

The initial tests on the electric pulse system looked promising. It was then decided the project warranted going to the next level.

The initial pilot test established baseline data. Heterotrophic plate count reductions and mold and yeast reductions were adequate.

Review of the metals data revealed the electrodes delivering the electric pulses were not migrating into the juice. There was no measurable increase in temperature, no pH change and no change in appearance of the juice.

3. Optimization of Technology for Treatment of Juices.

Two new 316L food grade stainless steel treatment chambers were built and placed in series. The chambers were constructed from an expanded pipe section, which involved dividing in half lengthwise a one foot section of 3 inch diameter stainless steel pipe, and joining upper and lower stainless steel expansion plates about one foot in length and about 7 inches in width to the respective pipe halves. End plates were then constructed and joined to each end of the expanded pipe section to create a chamber. Each end plate had a central opening for connection to 3 inch diameter inlet and outlet conduits. The construction using 3 inch conduit was sufficient to pass medium at a flow rate of 20 gpm. When constructed, the treatment chambers resembled automobile mufflers and were installed vertically to allow for draining. Two pairs of opposed cathode and anode electrodes insulated with one inch teflon insulators were installed through the end plates such that they were parallel to the inlet and outlet conduits, treatment chamber and flow path of the medium therethrough. The tips of the opposed cathode and anode electrodes were spaced about ¼ inch apart.

To best optimize the technology for treatment of juice, the system was installed in the production facility and evaluated as an integral part of the juice processing facility to determine not just its technical efficacy but to also to determine its practicality as a treatment component within a production facility.

While the new 316L food grade stainless steel chambers were being constructed, a complete review of the production facility was performed to determine the best installation location. It was determined the pulse modulation unit could be installed adjacent to other main electric components and the treatment chambers would be installed in the plant piping system so as to properly isolate the electric pulse process from the rest of the facility. The location chosen provided washing, grading, extraction, chilling, storage, bottling and a clean in-place disinfection system. A pulse frequency of 120 pulses per second was selected as being preferred based upon the pilot study tests.

4. Final Configuration of Technology.

Figure 2:
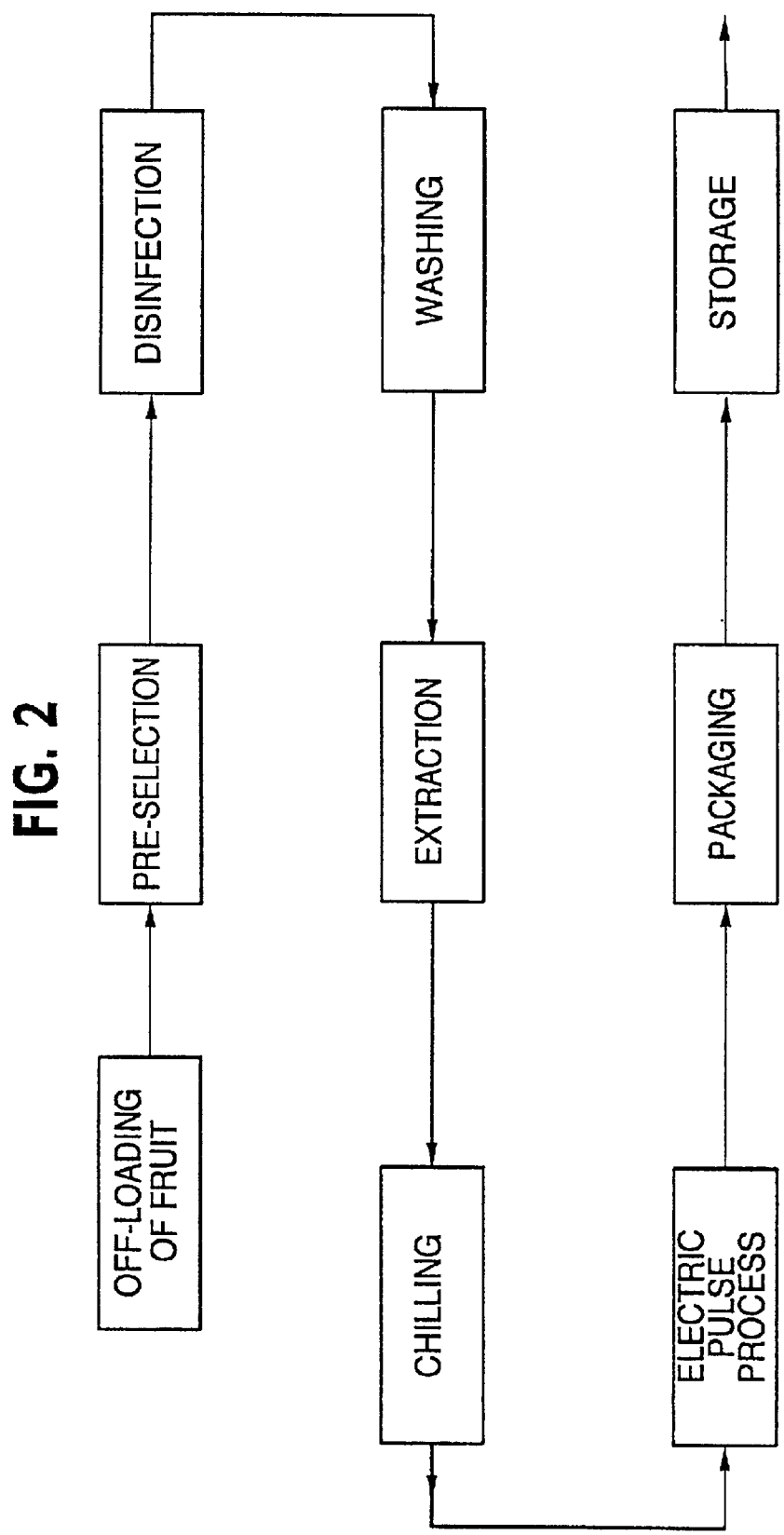
FIG. 2 shows a block diagram of a citrus juice processing system including the apparatus of this invention.

A block diagram of the final citrus juice process showing the location of the electric pulse process is shown in FIG. 2. The two 316L food grade stainless steel treatment chambers were mounted vertically in series.

The complete juice processing description is now described.

1. Off-loading of fruit
2. Pre-selection and culling to remove broken or damaged fruit
3. Disinfection of whole fruit exterior using approved food grade cleaning solutions
4. Washing of fruit using clean water
5. Extraction of juice
6. Chilling of juice
7. Application of electric pulses
8. Bottling of juice.
9. Storage of bottled juice It is further noted, as was determined during full scale testing, the use of the electric pulse process developed by the inventor as a treatment process for juices must be in conjunction with good manufacturing practices.

B. Full Scale Testing Program for Treatment of Juices

1. Testing Objectives

The pilot studies verified the electric pulse process of the invention was capable of meeting the product objective by reducing background micro-flora which resulted in a longer life product without altering its fresh juice characteristics. The process of the invention was next tested under actual operational conditions to evaluate the practicality of the process and study the treated juice product over a long period of time.

Additionally, it is noted that treated samples were analyzed by various groups within the citrus processing and marketing areas to evaluate the product as being viable to the consumers.

Several studies were planned to evaluate the treated juice products. Full scale exercises were necessary to determine the stability of the product over the period of time necessary to harvest, extract, pulse, bottle, and test. To evaluate the new 316L stainless steel chambers, metals were analyzed over time.

During the full scale testing phase, the treated juices were tasted by industry representatives for personal validation of the electric pulse process of the invention, and all materials of construction were examined to verify no food additives were being introduced into the juice.

The pulse modulation unit used (Model #PPS22) was a stand alone National Electric Code (N.E.C.) approved unit which was not located in a wetted environment. No pumpable food or juice product was capable of coming in process contact with this unit. The treatment chamber was the only portion of the electric pulse process which came in contact with the product to be treated. Therefore, the treatment chamber was evaluated.

During this phase of the project, it was concluded that all sampling for laboratory evaluation was to be done in sets of three. This was done to validate the data and also serve to verify laboratory procedures. Final validation of data for regulatory and industry review was accomplished in sets of seven.

2. Treatment Chamber Analysis

One of the main objectives in evaluating the electric pulse process was to determine if its application on juices was capable of creating a food additive which would exceed 0.5 ppb, which is The Threshold of Regulation by FDA. Another objective, equally as important, was to determine if its application on juices was capable of producing a product that would be safe and nutritious for the consumer.

The 316L stainless steel chambers were installed in the full production facility in an isolated production line. A series of initial tests were performed to test the chambers. Microbiological testing, juice characteristics and metals were analyzed. Adequate microbiological reductions were shown to have occurred, the juice characteristics were found not altered, and the metal analysis of the untreated and treated samples were found to be the same.

To further evaluate the treatment chambers, all materials of construction were examined. The wetted parts of the electric pulse treatment chambers are listed below with the materials of construction.

| Wetted Parts List Capable of Food Contact | | |
|---|---|---|
| Item | Material of Construction | |
| 1. Treatment chamber body | 316L SS with passavated welds | |
| 2. Connecting piping and flanges | 316L SS | |
| 3. Tubing | Tygon-Food grade | |
| 4. Electrode holder | Teflon-Food grade | |
| 5. Pressure gauges | 316 SS Food Grade | |
| 6. Electrodes: | Cathode | Anode |
| | 316 SS | 25% copper |
| | 16–18% Cr | 75% tungsten |
| | 10–14% Ni | |
| | 0.08% C | |
| | 2% Mn | |
| | 0.075% Si | |
| | 0.30% S | |
| | 2–3% Mo | |
| | 0.1% N | |

The review of wetted materials revealed all components were appropriate for food grade applications. The system was then tested to determine whether a migration of cathode and anode materials might have occurred. Metals analyses were performed which included the Primary and Secondary Standards for Metals in Drinking Water (as no metals standard for juice exists) and added to that list were any constituents which were in the materials of construction of the cathode and anode. Several tests were performed. It is specifically noted citrus juices naturally contain amounts of metals and minerals. The untreated samples varied in concentration for several constituents. The treated samples varied in concentration between the same values as the untreated samples. Therefore, it was concluded no migration of electrode materials had occurred.

Prior literature review had indicated in earlier years that electro-technology had difficulty in treating pumpable foods because of electrode erosion, free radicals and thermal heating.

None of these unacceptable elements had been detected in the full scale testing data. An examination of prior work in this field revealed previous pulsers used a great deal more energy, 150 joules/ml, to affect micro-organisms. Because of such great energy required, materials used in construction of the system were capable of migration. Additionally, large pulsers create heat as a result of the amount of energy applied. Large pulsers also have sufficient field strength to accelerate electrons to very high kinetic energy states. The high field strengths are required to cause electroporation of the cellular membrane of micro-organisms. Electroporation is one of the processes identified in the earlier literature review to cause microbial dysfunctionality in pulsed electro-technology.

The pulser used in this study was considerably smaller in its energy delivery than prior art pulsers. The data observed in pilot studies and initial chamber testing revealed that significant reductions in microorganisms did occur and at acceptable levels. The reductions in background microflora which included naturally occurring spoilage organisms stabilized the juice to acceptable levels.

The lower energy delivered to the juices was not creating additives. Additional literature review continued. Research chemists and microbiologists were consulted. Additional testing of the electric pulse process developed by the inventor on juices continued. Sufficient test runs were completed, samples collected and stored to analyze the juice over a two month period. Samples were opened and analyzed for acceptance to industry juice standards during this time frame. The juices, both grapefruit and orange, of many varietals and blends were analyzed during this phase. All products exhibited acceptable taste and appearance characteristics during this 60 day time frame.

During this time frame, the chambers were continually monitored for electrode wear. No visible or perceivable changes were detected in the electrodes.

It was concluded during this phase of work that the process of this invention was capable of lethal effects to micro-organisms.

To determine the potential for other effects to be generated with respect to the treatment of juices with electric pulses, a calculation of the energy density applied per chamber was performed and is shown below. The general form of the energy density equation (energy per unit volume) for a pulse treatment chamber is:

$$Ed = \frac{PRF \times Ep}{f}$$

where Ed is the pulse energy per unit volume (mj/ml), which is also referred to herein as the applied energy, Ep is the total energy per pulse delivered to the chamber (joules), PRF is the pulse repetition frequency (Hz), and f is the fluid flow rate.

For this specific system, we used two ¼ joule pulsers in a single chamber operating at 120 Hz and treating a fluid flow of 20 gpm. The energy density is found to be:

$$Ed = \frac{120 \text{ Hz} \times 2.0 \times 0.25 j}{20 \text{ gal/min} \times 3.78 \text{ liter/gal}}$$

$$Ed \text{ per chamber} = 47.6 \text{ mj/ml}$$

$$Ed = 47.6 \text{ millijoules per milliliter}$$

The low energy density explains the lack of electrode migration, why no temperature changes occurred and why no measurable or perceptible changes to the juice occurred due to the presence of free radicals. The energy densities and voltage potential of the field are not sufficient to cause changes. Further, laboratory results revealed no changes occurred in constituents analyzed in controls versus treated samples for metals and all juice related characteristics.

It was concluded during the treatment chamber evaluation, the use of two 316L stainless steel treatment chambers provided adequate reduction of background microflora to achieve the desired results in the juice without creating additives or altering the juice products.

It was then time to perform a shelf life study and metals analysis to validate the preliminary full scale testing results.

3. 28 Day Shelf-Life Study and Metal Analysis

A 28-day shelf life study and metals analysis was performed. The purpose of the study was to track untreated fresh juice control samples for 28 days and determine its rate of spoilage, and compare treated samples for spoilage time frames.

Additionally, samples were analyzed for fresh juice characteristics. Temperature, pH and flow rates were recorded and sufficient treated samples were collected to perform in-house analysis beyond the 28-day validation tests. Also metals were analyzed to validate no migration of materials of construction had occurred.

All sampling was performed by independent laboratories. Air quality and sample containers were analyzed during the collection of all samples.

The shelf life study revealed the control samples spoiled between 21 and 28 days. The treated samples were evaluated by tracking standard plate counts (SPC). The SPC of the treated samples at day 28 was less than the original untreated plate count control on day one. Additionally, mold and yeast treated sample values were also less at day 28 than untreated plate count controls on day one.

Stored treated samples were opened after 30, 60 and 90 days and were still acceptable. It should be noted samples were stored in conventional consumer bottles at 45° F.

Also evaluated during the shelf-life study were *E. coli*, total and fecal coliform, and Salmonella. A naturally existing organism in the background microflora of juice is Klebsiella. It gives a false fecal coliform reading. Klebsiella appeared in all control samples through the 28-day shelf-life study but did not appear in any of the treated samples. The electric pulse process also eliminated this organism.

The metals analysis revealed the control samples metal constituent values varied slightly. The treated sample values varied in the same fashion.

It was concluded the variations in metals concentrations were a result of the variations in the actual juice, not as a result of any changes created by the electric pulse process. This data was consistent with previous data. This conclusion was also supported by subsequent tests.

After review of this data and discussion of the data with other industry experts, it was concluded the full scale testing phase met the test objectives.

4. Proposed FDA Juice Labeling Rules

During the development of the final testing program for validation and submittal to FDA, proposed Juice Warning Label Rules were published Apr. 24, 1998 (Volume 63, Number 79).

A review of the proposed rule indicated a five log reduction in target pathogen organisms would be required to be validated in all juice products labelled as "Fresh" or a warning label would be mandated for the product. Additionally, the target organisms were identified in the proposed rule to be *Listeria monocytogenes* and *E. coli* 0157:H7. It was contemplated to expand the final pathogen testing program to include these organisms.

C. Final Testing Program for Treatment of Juices and Milk

1. Testing Objectives

The final testing phase of the project was developed to 1) demonstrate conclusively the efficacy of the electric pulse process at providing a five log reduction of target pathogenic organisms in juices; 2) subject treated juices to an independent organo-leptic testing panel to verify no changes in the juice product could be perceived; and 3) perform final metals evaluation of treated vs. non-treated juices to verify no changes in metal concentrations were occurring as a result of using the electric pulse process.

Additionally, it was decided to perform pathogen reduction testing of target organisms occurring in milk. The exercise was performed to verify the electric pulse process' ability for microbial reduction in low acid products.

Although the proposed juice label warning rule identified Listeria and *E. coli* 0157:H7 as target pathogens, it was also felt the electric pulse process needed to be tested over a wider range of organism types.

This was believed necessary to demonstrate to industry representatives the process is applicable to other pathogens. And, as certifications are required, the inventor wanted additional reasonable assurance as to the efficacy of the electric pulse process prior to final certifications.

The following portions of this section will present the final data related to testing prior to preparation of submittals.

2. Pathogen Testing (1) Juice

A full scale pathogen testing program was designed to validate the electric pulse process's ability to achieve a five log reduction in pathogenic organisms.

After discussions with microbiologists, it was concluded the safest testing location would be at the laboratory under very controlled conditions. Demonstrating a five log reduction required spiking juice with known concentrations of organisms to a 10 log concentration and measuring reductions.

A full scale 20 gpm, dual chamber system was taken to the independent laboratory in Orlando, Fla. and readied for testing. The laboratory obtained the selected organisms. At this phase of validation, it had been agreed all tests would be conducted in sets of seven. Because of the volume of juice required to cover the list of organisms and the number of samples which physically had to be analyzed, it was agreed final testing would occur in three separate sessions.

The production facility and the laboratory were located in different cities. Good coordination of juice extraction and containerization, transportation and refrigeration as well as technicians, and laboratory personnel was essential.

At each testing session, the juice was extracted and refrigerated as during all other phases of this project. The juice was then transported via refrigerated truck to the laboratory. Juice was transported in 47 gallon, lined and sealed containers. All work was performed in a certified laboratory and supervised by qualified individuals.

The Bacteriological Analytical Manual was used for all laboratory work. Disposal of all contaminated materials was performed by a certified hazardous waste disposal contractor.

All tests were conducted to simulate the same conditions as had been used to analyze the electric pulse process in both the pilot scale and full scale testing.

The target pathogens inoculated and tested in fresh citrus juices are listed below.

Target Pathogens to be Tested in Citrus Juice Using Electric Pulse Process for Microbial Reduction 1. *Listeria monocytogenes*
2. *Clostridium sporogenes*
3. *Salmonella typhimurium*
4. *Lactobacillus lactus*
5. Endotoxin
6. *E. coli* 0157:H7
7. *Aspergillus niger*
8. *Penicillium digitatum*

All samples were treated at 20 gpm, using two 316L stainless steel electric pulse treatment chambers in vertical series at a pulse rate of 120 Hz at ½ joule/ml per chamber. Juice was pumped from each individually inoculated 47 gallon barrel through the treatment chambers and samples were taken on the discharge line. This procedure was performed each time a new organism was tested for reductions using the electric pulse process.

The reduction testing for validation on Listeria, Clostridium, Salmonella, Lactobacillus and Endotoxin was performed. A laboratory validation report for these pathogenic organisms was prepared. The summary of log reductions for the data sets for these organisms is included herein below in part (3) of this Section titled "Summary of Log Reductions for Target Pathogenic Organisms". The additional pathogenic organisms tested in juice were *E. coli* 0157:H7, *Aspergillus niger* and *Penicillium digitatum*. These organisms were tested for reductions using the electric pulse process. A laboratory validation report for these organisms was prepared. The summary of log reductions for the data sets for these organisms is also included herein below in part (3) of this Section.

It is specifically noted that *E. coli* 0157:H7 has been identified as a resistant organism to any disinfection method. As a result this particular pathogen was subjected to electric pulses with samples taken and then the treated juice was pulsed a second time. This was done to determine if additional reductions could occur by treating juice using four chambers. The results of the tests demonstrated that pulsing the juice a second time resulted in an additional log value reduction of microorganisms.

All reductions in pathogens inoculated in juice and treated using the electric pulse process with two chambers in series resulted in a five log or greater reduction. Additionally, and considering the log spike concentration recovered, $10^9$ CFU/gal, in most cases, the actual organism reductions were greatly in excess of 100,000-fold reductions.

(2) Milk Testing

The application of the electric pulse process of the invention to milk is intended to show efficacy of the process for pathogenic reductions in a different pH food. Raw milk and its target pathogens represents a reasonable example of a different food type and micro-organism problem. *Streptococcus faecalis* and *Bacillus cereus* were tested under the same electric pulse process conditions described above as juice. Raw milk was obtained, inoculated and tested in the same fashion as the juice. The test was performed and a report was prepared.

The summary of log reductions for pathogens tested in milk is shown in part (3) of this Section. From the data, it is concluded all pathogens tested were reduced by five log or greater. This further validated the electric pulse process' ability to reduce target pathogens in a different pH food.

(3) Summary of Log Reductions for Target Pathogenic Organisms

The data collected for validation of the electric pulse process is extensive. All validation sampling was performed in sets of seven. In review of the data, the log reductions in target pathogens were consistent by organism. All organisms tested were reduced by at least five log, a very impressive reduction considering the starting organism concentration levels which were tested in the samples.

As all log reductions for each organism set were the same, only one value is shown in the following summary tables.

Summary of Log Reductions for Target Pathogenic Organisms in Juice

| | Organism | Log Reduction-Set Average |
|---|---|---|
| 1. | *Listeria monocytogenes* | 7 log |
| 2. | *Clostridium sporogenes* | 8 log |
| 3. | *Salmonella typhimurium* | 7 log |
| 4. | *Lactobacillus lactus* | 7 log |

-continued

Summary of Log Reductions for Target Pathogenic Organisms in Juice

| | Organism | Log Reduction-Set Average |
|---|---|---|
| 5. | Endotoxin | 5 log |
| 6. | *E. coli* 0157:H7 | 5 log |
| 7. | *Aspergillus niger* | 7 log |
| 8. | *Penicillium digitatum* | 7 log |

Summary of Log Reduction for Target Pathogenic Organisms in Milk

| | Organism | Log Reduction-Set Average |
|---|---|---|
| 9. | *Streptococcus faecalis* | 6 log |
| 10. | *Bacillus cereus* | 7 log |

The data summarized herein indicates the electric pulse process is capable of reducing a wide range of organisms in different types of conductive media.

3. Organo-Leptic Testing

Test samples were subjected to an organo-leptic evaluation by a sensory panel, to demonstrate that no food additives were created or added by the electric pulse process or its materials of construction, and to demonstrate that the treated juice could not be distinguished from untreated fresh squeezed juice. A report of the organo-leptic evaluation was prepared.

The conclusion drawn by the sensory report is that there were no distinguishable differences between the treated and untreated samples. The panel liked both the treated and untreated samples, and both samples received high relative scores.

4. Metals Testing

The final evaluation was a metals analysis. There are no published standards for juices. The constituent list chosen for final analysis for metals is the U.S. Public Health Standards for Drinking Water plus the materials of construction for the electrodes not identified in the USPHS. It was considered this list would be representative of all constituents which could be expected to change if, in fact, changes were to occur.

It has been mentioned above that there does not appear to be sufficient energy present at application to change the energy states of molecules in solution. The process appears to only provide sufficient energy at a specific pulse shape and pulse repetition rate to lethally affect the microorganisms without effecting the medium.

The examination of metals therefore, represented the last examination related to potential food additives.

The samples for analysis were collected in sets of seven for final validation. The samples were collected from the same extraction run performed to supply juice for the pathogen testing described above. A metals analysis was prepared.

Review of the data reveals fresh squeezed untreated (raw) citrus juices contain metals and minerals. Specifically, barium, copper, iron, manganese, nickel, sodium, tungsten, and zinc were identified in the raw juice. The metals analysis revealed the untreated juice control samples varied between specific concentrations. The treated samples also contained the same concentrations of metals as the untreated samples, with the exception of two iron values, and varied in the same fashion as did the untreated samples. A literature review was performed to determine published ranges of these constituents in raw juice. All concentrations in the raw juice and treated samples were within published ranges including iron. The iron values varied in every sample. Two iron values in the treated samples were 0.02 mg/l and 0.04 mg/l higher than the control sample variations. However, it is believed the slightly higher iron values were as a result of the varying concentrations in the raw juice, as no iron components are part of this electric pulse process. A comparison of published ranges of constituents were made to the data reported herein. Concentrations of copper, iron, manganese, sodium and molydbium identified in the control samples were within the ranges reported in published literature. No published values for barium, nickel or tungsten were found by the inventor.

It was concluded the background control values were, in fact, elements of the juice. The reported values for the treated samples varied within the same values as the untreated juice. It was concluded, no changes in metal concentrations had occurred as a result of treating the juice with the electric pulse process of the invention.

The above described preferred embodiments illustrate the principles of the invention but are not intended to limit the scope of the invention. Variations to these embodiments will be apparent to those skilled in the art and may be made without departing from the scope of the following claims:

I claim:

1. A process for reducing microorganisms in a conductive medium, which comprises subjecting the medium containing microorganisms to low voltage pulsed electrical energy, the low voltage pulsed electrical energy being generated by a pair of electrodes contacting the medium and having a defined voltage, the low voltage pulsed electrical energy having a defined frequency and defined waveform, wherein the pulsed electrical energy forms no free radicals, creates no osmotic shock, and generates no ionizing radiation, wherein the pulsed electrical energy causes no detrimental change to the conductive medium, and wherein the pulsed electrical energy reduces the microorganisms in the medium, provided that the conductive medium is not a pumpable food or beverage.

2. The process according to claim 1, wherein the conductive medium is blood.

3. The process according to claim 1, wherein the conductive medium is a conductive solid.

4. The process according to claim 1, wherein the conductive medium is a liquid or gas containing contaminated solids which are suspended or immersed in the liquid or gas.

5. The process according to claim 1, wherein the frequency of the pulsed electrical energy is in a range of 1 to 1000 pulses per second.

6. The process according to claim 1, wherein the frequency of the pulsed electrical energy is about 120 per second.

7. The process according to claim 1, wherein the pulse waveform has a shape which is a monopulse in the positive domain.

8. The process according to claim 1, wherein the pulse waveform has an amplitude in a range of 6,000 V to 15,000 V.

9. The process according to claim 8, wherein the pulse amplitude is about 12,000 V.

10. The process according to claim 1, wherein the microorganisms in the conductive medium are reduced by about 5 log or more after treatment.

11. The process according to claim 1, wherein the medium containing microorganisms is subjected to the electric energy pulse while the medium is passed through a treatment space.

12. The process according to claim 11, wherein the medium is passed through the treatment space at a flow rate of 1 to 300 gallons per minute.

13. The process according to claim 12, wherein the flow rate of medium is in a range of 15 to 25 gallons per minute.

14. The process according to claim 11, wherein the treatment space is equipped with one or more pairs of electrodes connected to one or more pulser units for generating an electrical energy pulse.

15. The process according to claim 11, wherein the treatment space is equipped with two or more pairs of electrodes connected to two or more pulser units for generating two or more respective electrical energy pulses.

16. The process according to claim 15, wherein the two or more electric energy pulses generated by the two or more pairs of electrodes connected to two or more respective pulser units have a different pulse frequency, different pulse shape, and/or different pulse amplitude, for the treatment of one, two or more different types of microorganisms contained in the medium.

17. The process according to claim 15, wherein the two or more pulser units subject the microorganisms contained in the medium to different levels of applied energy.

18. The process according to claim 11, wherein the medium is passed through a plurality of two or more treatment spaces, each treatment space being equipped with at least one pair of electrodes connected to at least one pulser unit for generating an electrical energy pulse.

19. The process according to claim 11, wherein the treatment space is within a conduit.

20. The process according to claim 11, wherein the treatment space is within a chamber.

21. The process according to claim 1, wherein the low voltage pulsed electrical energy subjects the microorganisms to an applied energy of less than or up to 1 joule per milliliter.

22. The process according to claim 1, wherein the flow rate is less than 1 gallon per minute.

23. The process according to claim 1, wherein the low voltage pulsed electrical energy subjects the microorganisms to an applied energy of greater than 1 joule/ml.

24. A conductive medium which is treated by the process according to claim 1, provided that the conductive medium is not a pumpable food or beverage.

25. The conductive medium according to claim 24, which is blood, wastewater, a conductive solid or a suspended solid.

26. A process for killing a specific target microorganism in a conductive medium, which comprises
(a) subjecting the medium containing the specific target microorganism to an electric energy pulse having a predetermined pulse waveform and predetermined pulse frequency, thereby subjecting the microorganism to a predetermined applied energy,
(b) measuring the effectiveness of the electrical energy pulse on killing the microorganism,
(c) adjusting one or more of the pulse waveform, pulse frequency, or applied energy of the electric energy pulse,
(d) subjecting the medium containing the microorganism to the adjusted electric energy pulse,
(e) measuring the effectiveness of the adjusted electric energy pulse on killing of the microorganism, and
(f) optionally repeating steps (c), (d) and (e) to determine the optimum pulse waveform, pulse frequency and applied energy to kill the microorganism provided that the conductive medium is not a pumpable food or beverage.

27. The process according to claim 26, wherein the medium containing the microorganism is subjected to the electric energy pulse by passing the medium containing the microorganism through an energy pulser treatment space at a predetermined flow rate.

28. The process according to claim 27, wherein the flow rate of the medium containing the microorganism is also adjusted to optimize killing the microorganism.

29. The process according to claim 26, wherein the specific target microorganism is a member selected from the group consisting of Listeria, Clostridium, Salmonella, Lactobacillus, Endotoxin, *E. coli, Aspergillus niger*, Penicillium, Streptococcus, Bacillus and Klebsiella.

30. A conductive medium which is treated by the process according to claim 26, provided that the conductive medium is not a pumpable food or beverage.

31. The conductive medium according to claim 30, which is blood, wastewater, a conductive solid or a suspended solid.

32. An apparatus for the treatment of a conductive medium containing microorganisms, which comprises a first conduit for passing the conductive medium therethrough, said first conduit connected in flow path arrangement to a treatment space for passing the conductive medium into the treatment space, the treatment space being equipped with an electric energy pulser for treating the microorganisms with an applied energy, and a second conduit connected in flow path arrangement to the treatment space for passing the treated medium out of the treatment space, wherein the conductive medium is not a pumpable food or beverage.

33. The apparatus according to claim 32, wherein the first conduit is equipped with at least one sensor for monitoring the pH, pressure, temperature, conductivity and/or flow rate of the conductive medium.

34. The apparatus according to claim 32, wherein the second conduit is equipped with at least one sensor for monitoring the pH, pressure, temperature, conductivity and/or flow rate of the conductive medium.

35. The apparatus according to claim 32, wherein the electric energy pulser is equipped with at least one sensor for monitoring the current, voltage, pulse shape and/or pulse frequency.

36. The apparatus according to claim 32, wherein the treatment space is within a conduit or chamber.

37. The apparatus according to claim 32, which includes at least one control for adjusting the pulse frequency, pulse shape, pulse amplitude or pulse voltage.

38. A conductive medium which is treated with the apparatus according to claim 32, wherein the conductive medium is blood, wastewater, a conductive solid or a suspended solid.

* * * * *